(12) United States Patent
Shen

(10) Patent No.: US 8,606,601 B2
(45) Date of Patent: Dec. 10, 2013

(54) APPARATUS AND METHOD OF AUTOMATED INFORMATION EXTRACTION AND IMPLEMENTATION THROUGH LARGE SCALE NETWORKS

(76) Inventor: Michael Shen, Ft. Lauderdale, FL (US)

(*) Notice: Subject to any disclaimer, the term of this patent is extended or adjusted under 35 U.S.C. 154(b) by 125 days.

(21) Appl. No.: 13/004,953

(22) Filed: Jan. 12, 2011

(65) Prior Publication Data
US 2011/0184760 A1 Jul. 28, 2011

Related U.S. Application Data

(60) Provisional application No. 61/294,345, filed on Jan. 12, 2010.

(51) Int. Cl.
*G06Q 10/00* (2012.01)

(52) U.S. Cl.
USPC .......................................... 705/3; 705/216

(58) Field of Classification Search
USPC ............................................................ 705/3
See application file for complete search history.

(56) References Cited

U.S. PATENT DOCUMENTS

| | | | |
|---|---|---|---|
| 6,772,160 B2* | 8/2004 | Cho et al. ................... | 702/84 |
| 2002/0103811 A1* | 8/2002 | Fankhauser et al. ........ | 707/104.1 |
| 2002/0165737 A1* | 11/2002 | Mahran ....................... | 705/3 |

* cited by examiner

*Primary Examiner* — Hiep V Nguyen
(74) *Attorney, Agent, or Firm* — Cahn & Samuels, LLP

(57) ABSTRACT

A system and method for extracting medical information into a digital format; classifying the medical information into a database with customizable standard categories; and implementing the new information on all related customers' system in large scale networks.

3 Claims, 19 Drawing Sheets

Functional Design of Data Extraction

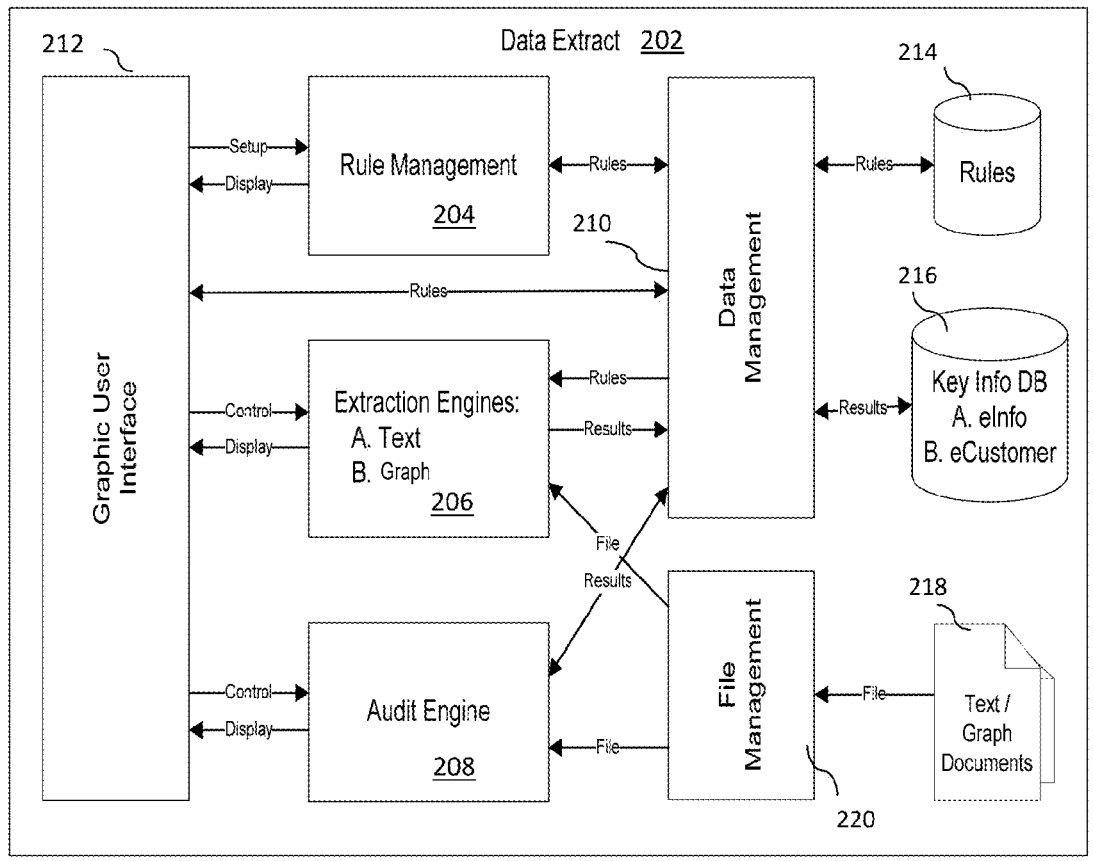
FIGURE 2 Functional Design of Data Extraction
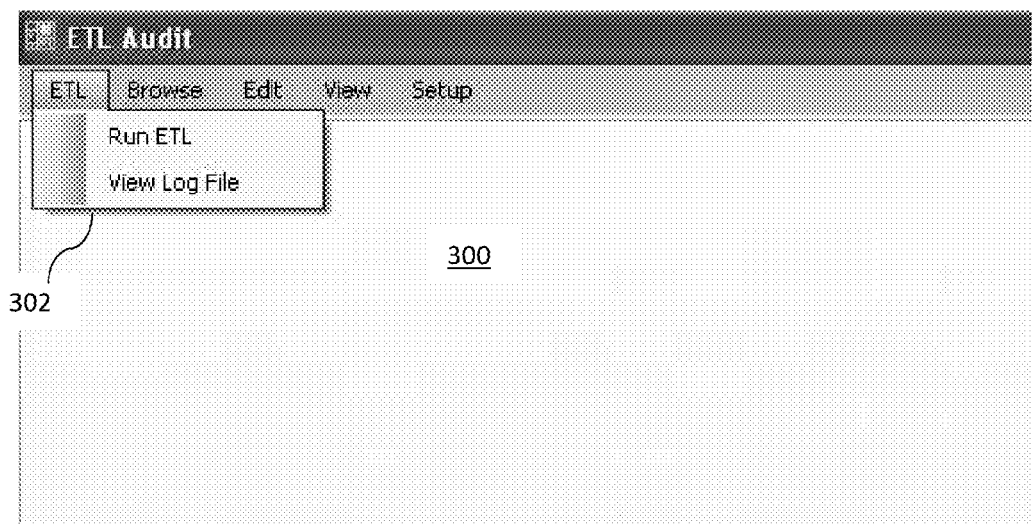
Figure 3 Screen Capture of Text Extraction Engine 400
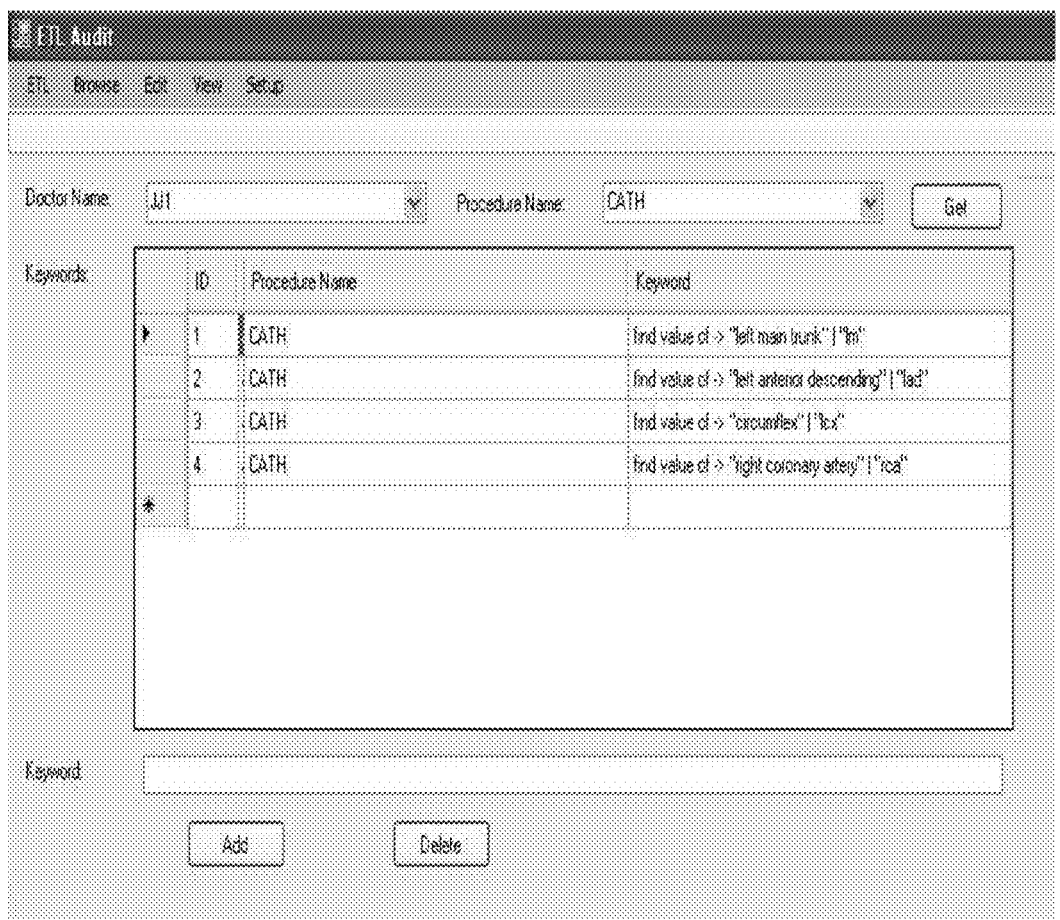
Figure 4 Screen capture for Keywords Setup

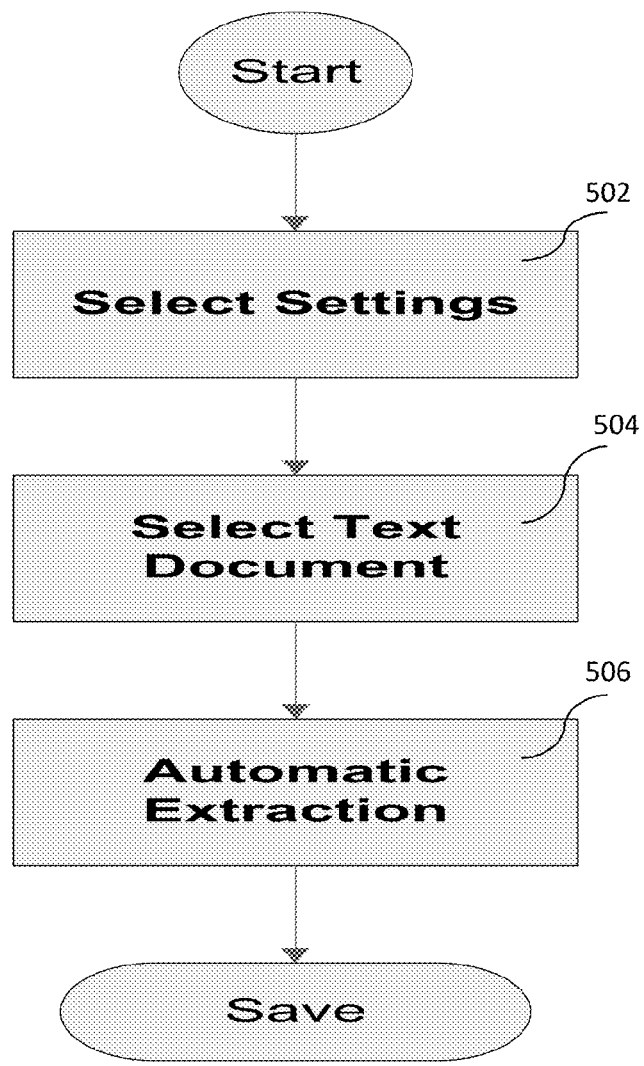
Figure 5 Three Major Steps in Text Extraction stage

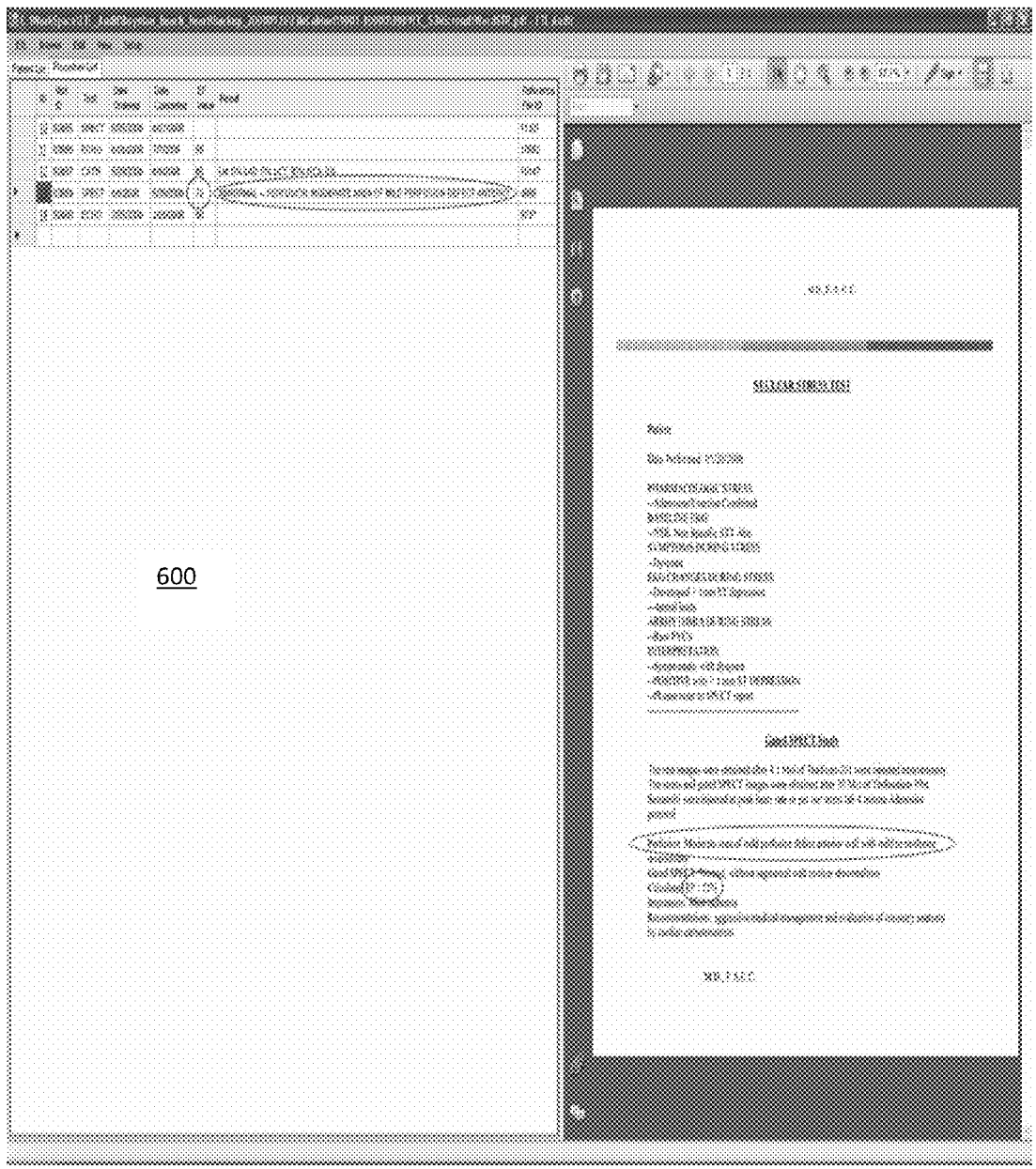
Figure 6 Screen Capture for Text Extraction Results

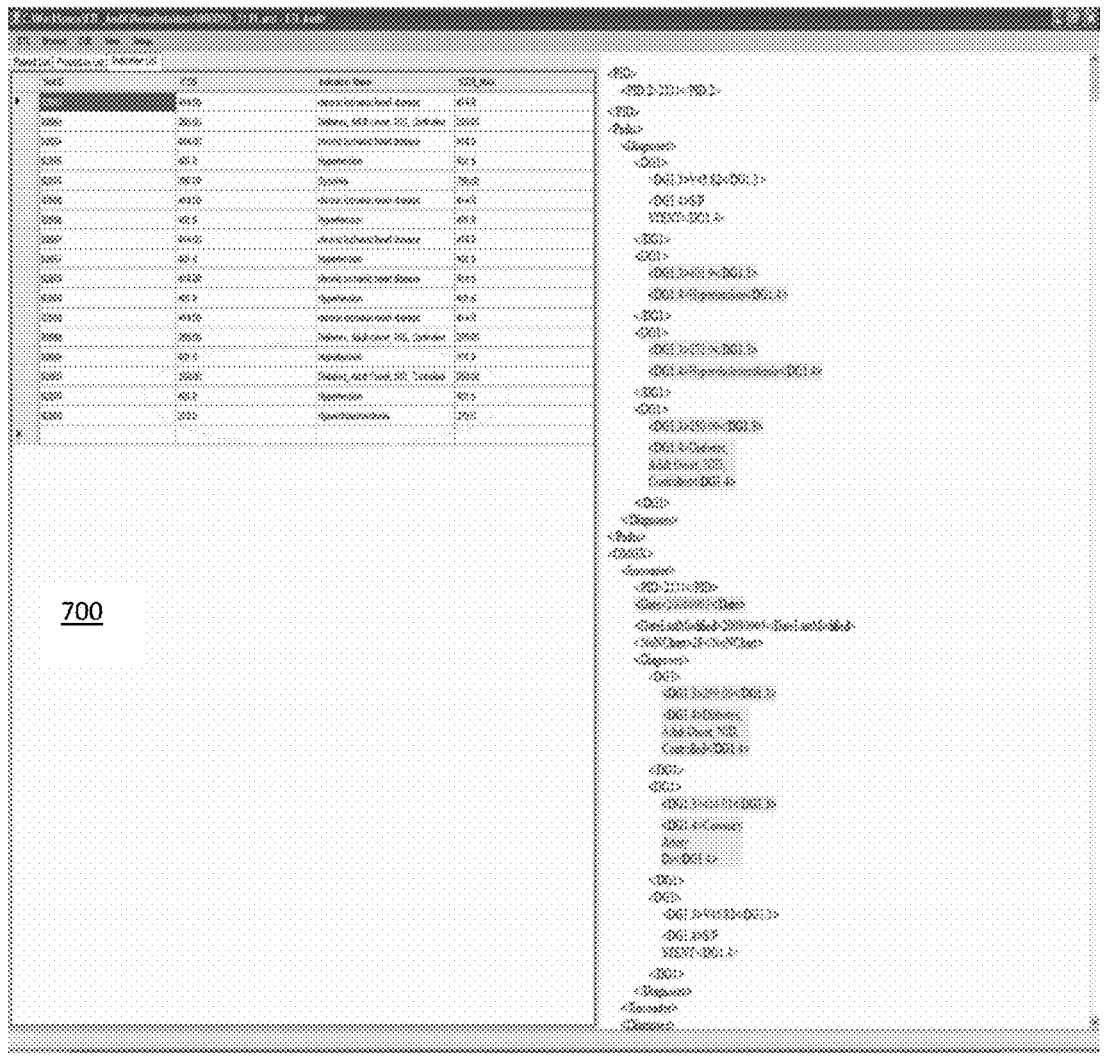
Figure 7 Screen Capture for Audit Screen

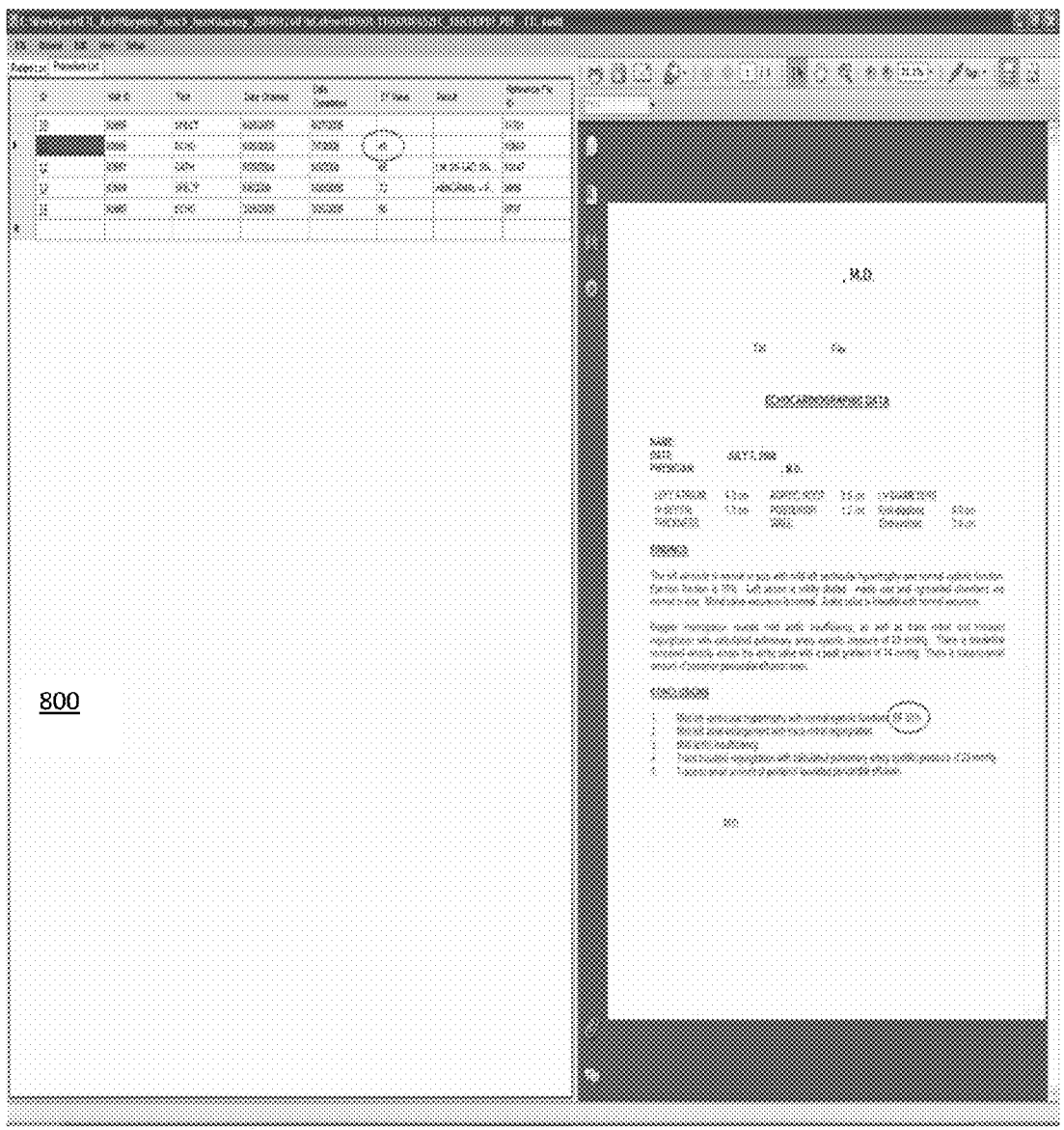
Figure 8 Screen Capture for Audit Screen: incorrect data found

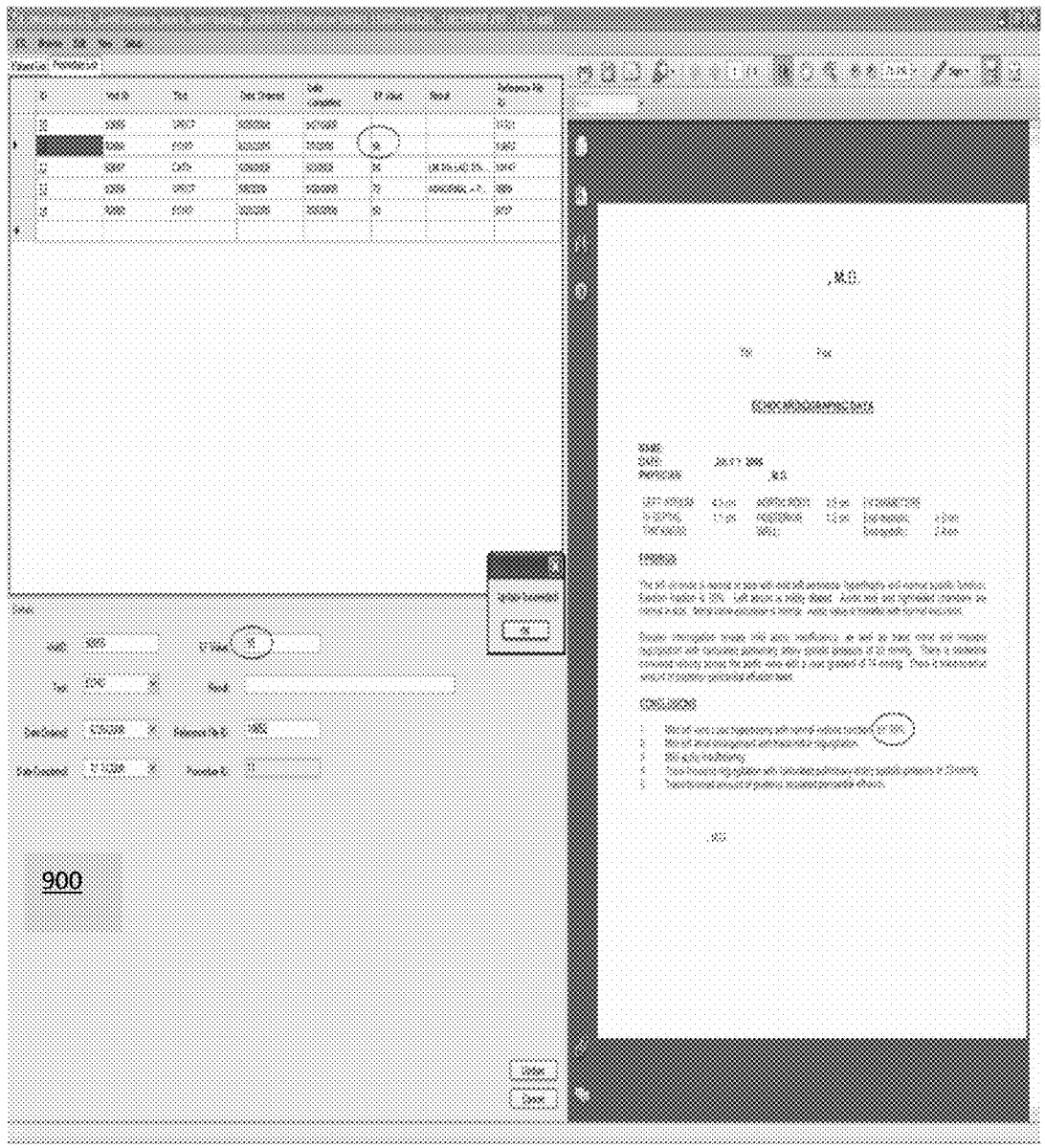
Figure 9 Screen Capture for Audit Screen: incorrect data fixed

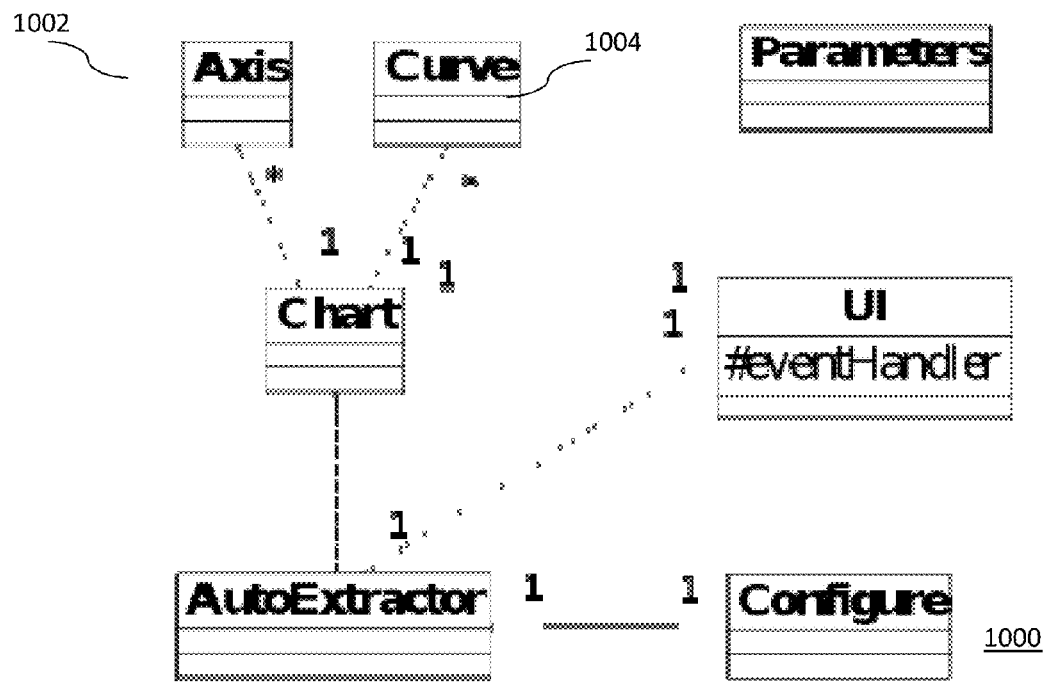
Figure 10 Functional Design of Graphic Extraction Engine
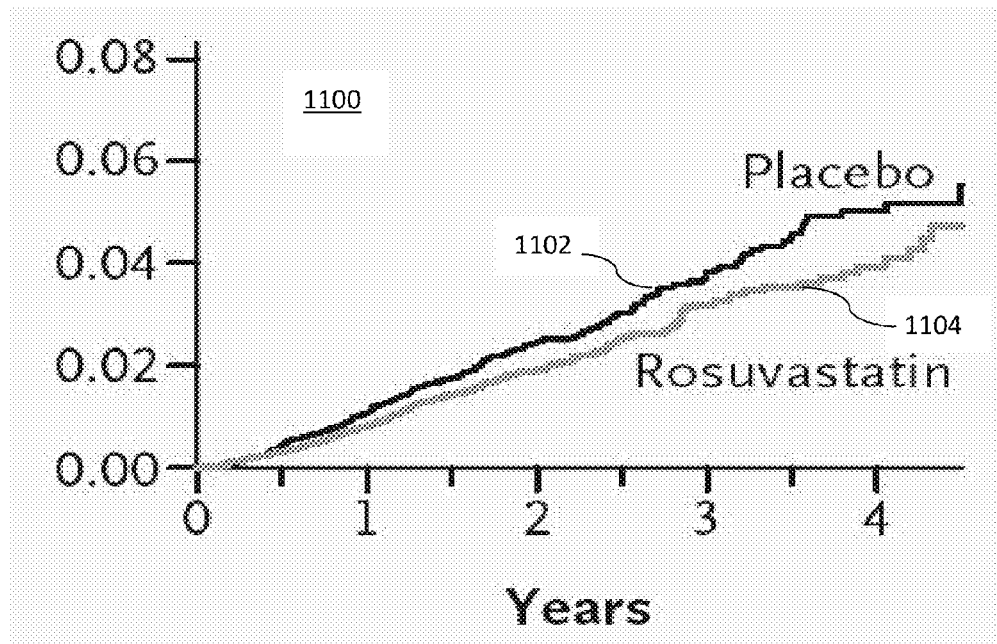
Figure 11 Sample image chart retrieved from a research paper

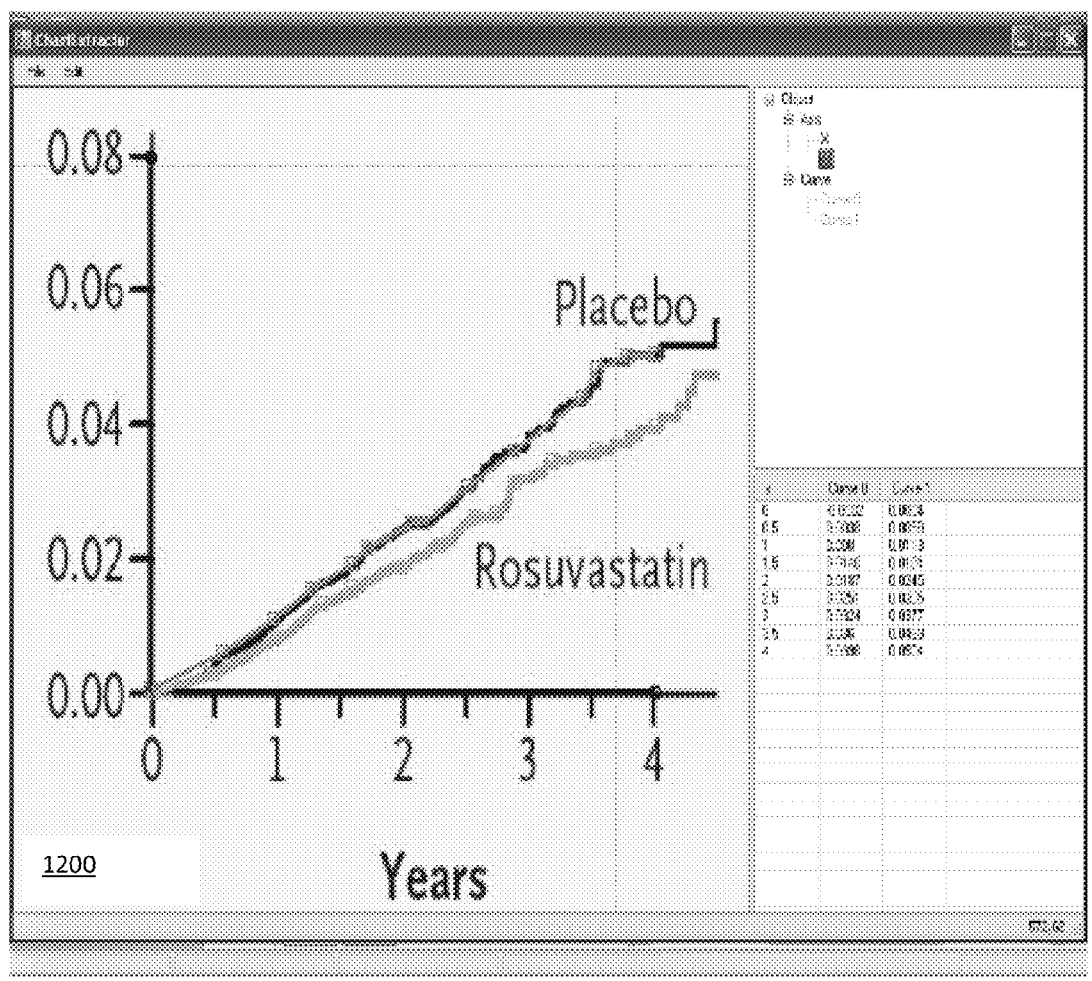
Figure 12 sample screen capture of Graphic Extraction Engine user interface

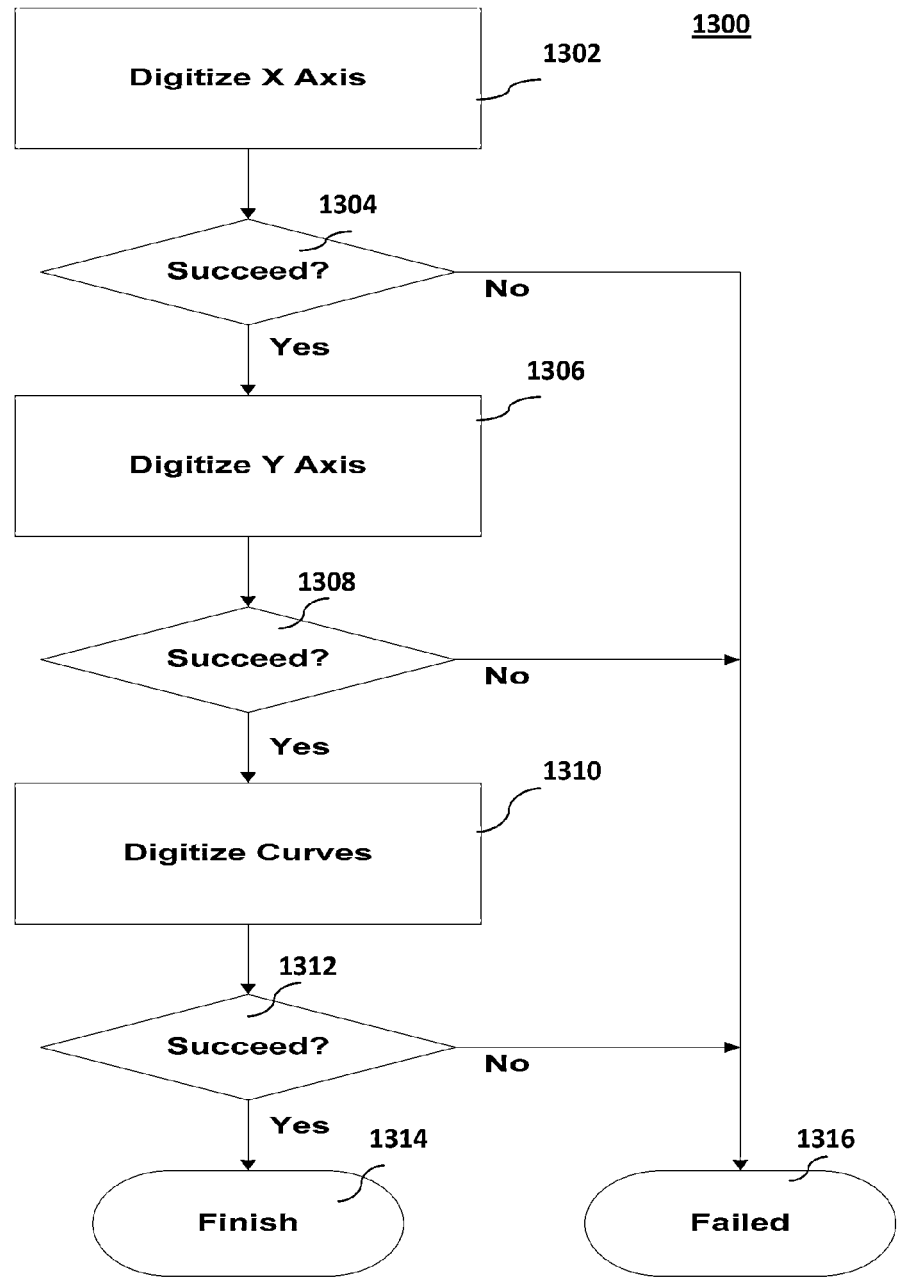
Figure 13 Work flow of automatic graphic extraction

1400
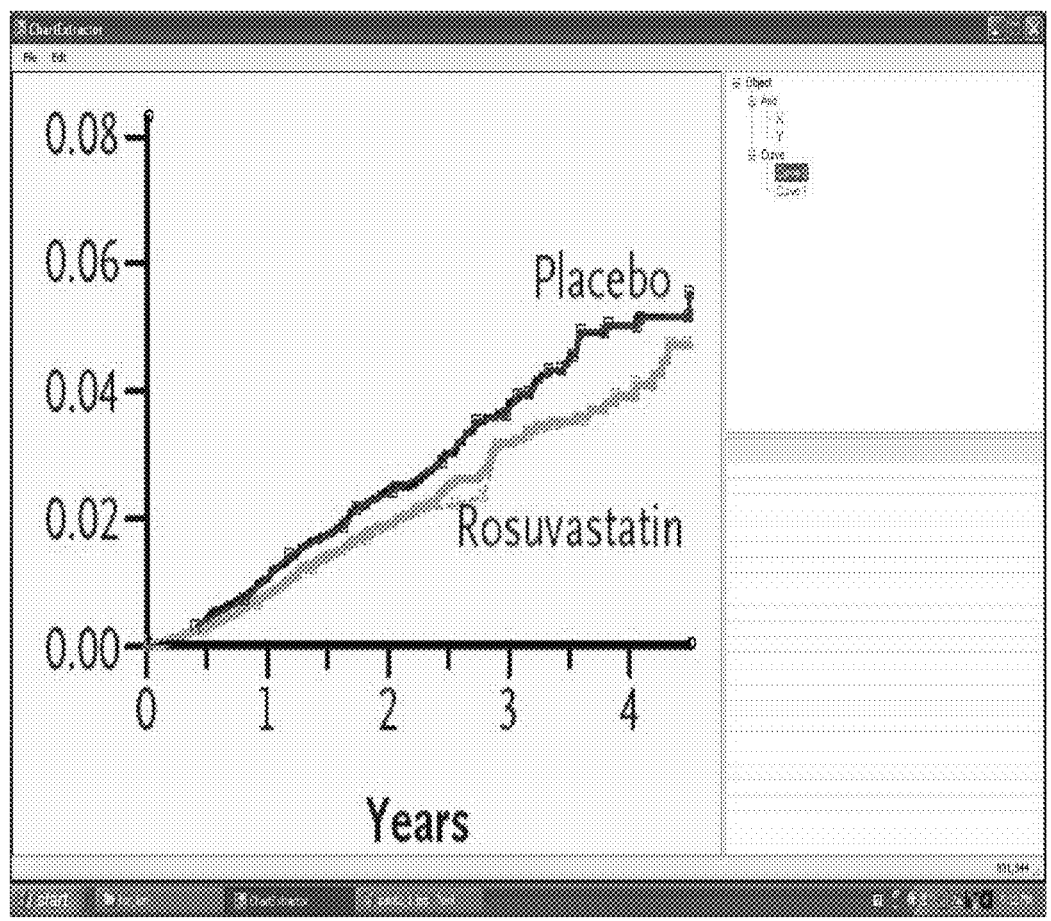
Figure 14 Sample digitalized graphic chart before manual adjustment

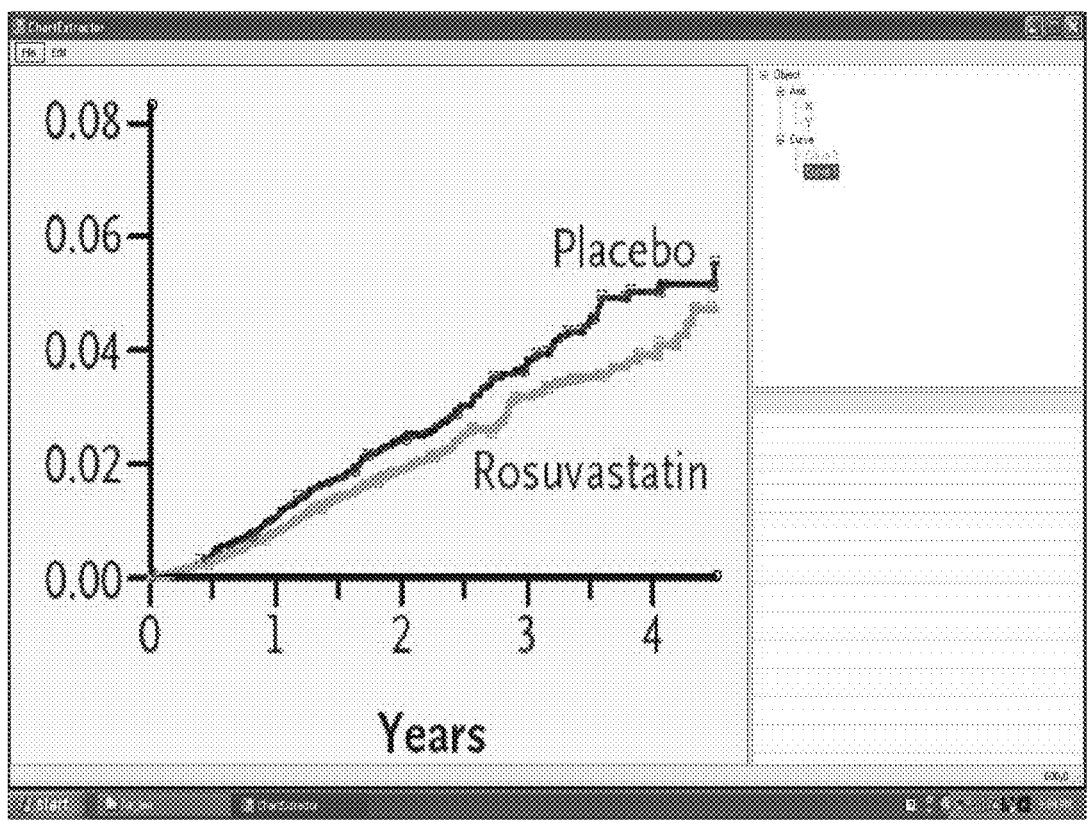
Figure 15 Sample digitalized graphic chart after manual adjustment

1600
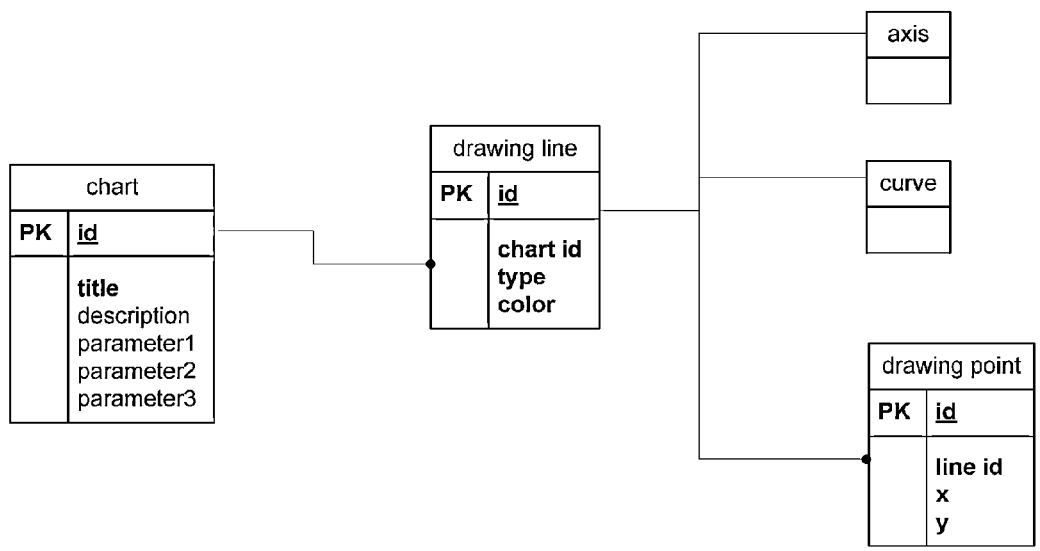
Figure 16 Database schemas for Key Info

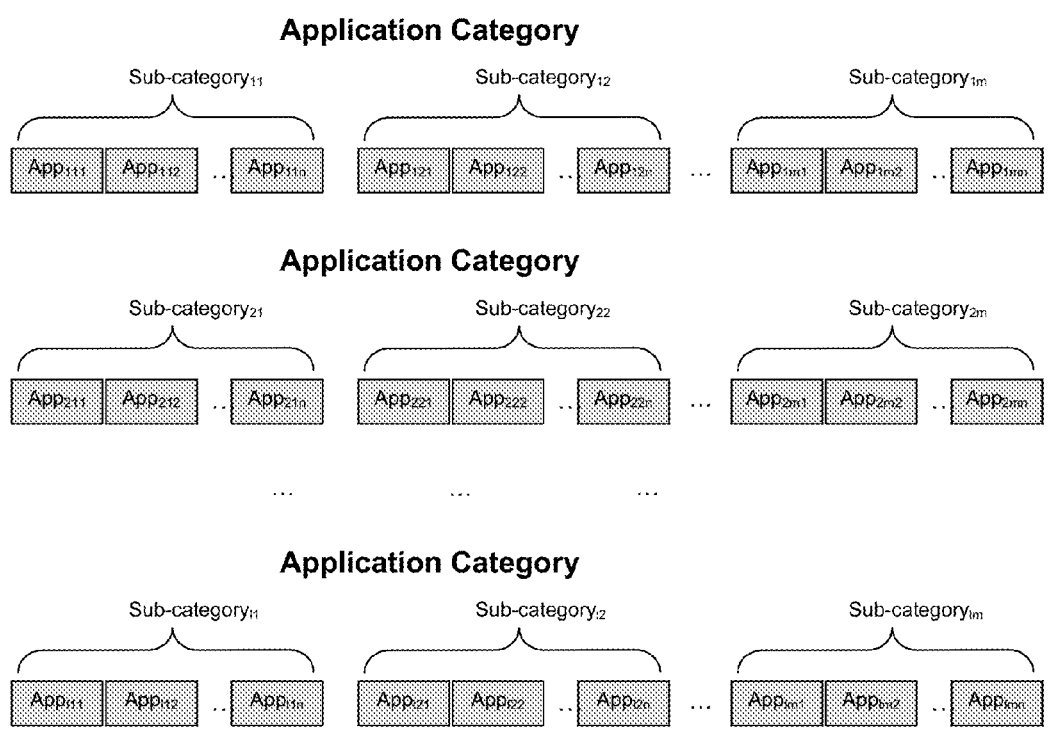
Figure 17 Data Category and Application

1800
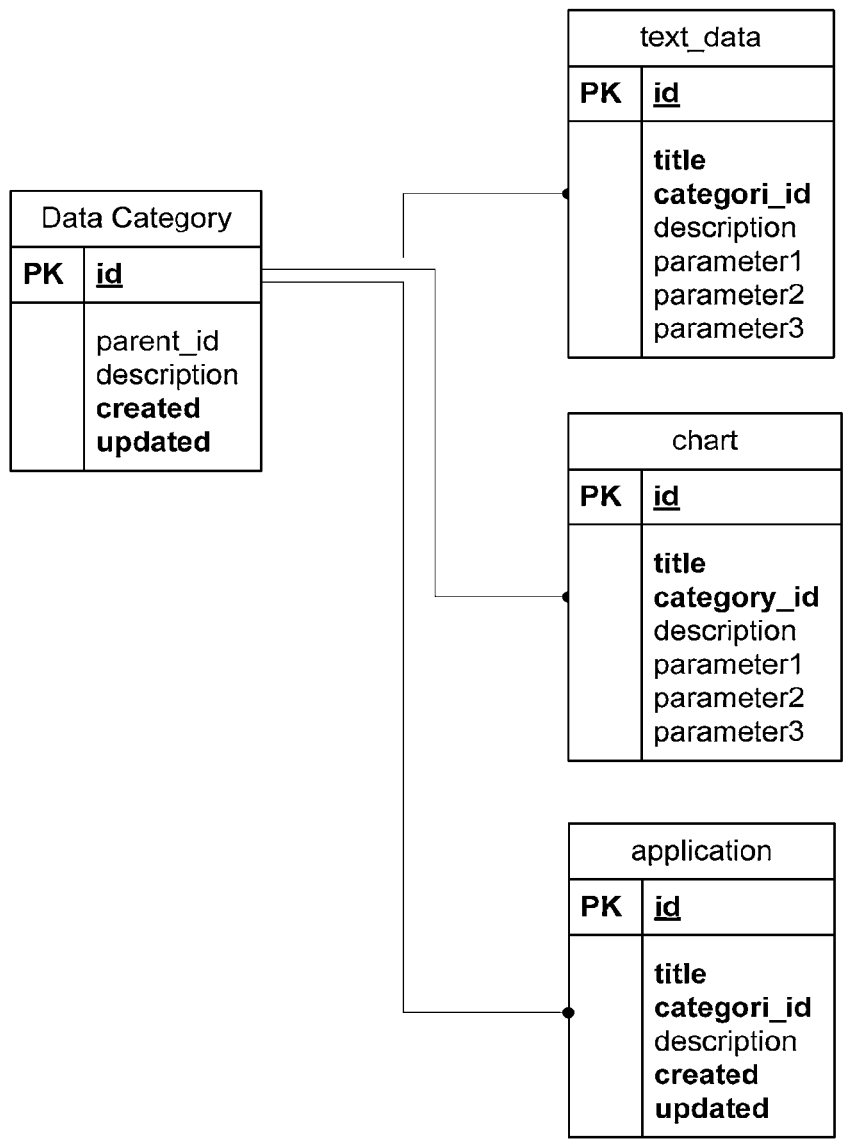
Figure 18 Database Schemas for Data Sets, Data Categories and Applications

1900

1950

APPARATUS AND METHOD OF AUTOMATED INFORMATION EXTRACTION AND IMPLEMENTATION THROUGH LARGE SCALE NETWORKS

CROSS-REFERENCE TO RELATED APPLICATIONS

This application is a non-provisional of, and claims priority from, application Ser. No. 61/294,345 filed on Jan. 12, 2010, which is incorporated by reference herein.

FIELD OF THE INVENTION

The present invention relates to information management and more specifically to management of medical information.

BACKGROUND OF THE INVENTION

It is challenging to automatically implement new information, to customers' systems immediately in large scale networks. For example, it is estimated that it may take up to seventeen years to implement a new treatment (as a new technology or medication) in healthcare, to reach only 50% of use in the indicated patients. The results of this slow implementation process can significantly impact on patients' outcomes and healthcare costs. An improvement is required in collecting and implementing the new information.

SUMMARY OF THE INVENTION

Briefly, according to an embodiment of the invention, a method includes steps or acts of: extracting medical information into a digital format system; classifying the medical information into an information database with customizable standard index categories; converting patient information into a digital format from all related medical information system; classifying patient information into a patient database with standardized index categories; and implementing the new information to all patients based on related indexed categories through related medical information system in large scale networks; display, suggesting/guiding, and notifying performance improvement comparing real patient information with related medical information based on indexed categories at the point of care using variety evaluation or outcome tools; using a customizable rule-based system with auditing modification to automated the information extraction, implementation and performance improvement process.

BRIEF DESCRIPTION OF THE SEVERAL VIEWS OF THE DRAWINGS

To describe the foregoing and other exemplary purposes, aspects, and advantages, we use the following detailed description of an exemplary embodiment of the invention with reference to the drawings, in which:

FIG. 2 shows a functional design of a data extraction (Text or Graphic), according to an embodiment of the present invention;

FIG. 3 is a screen capture of the Text Extraction Engine extract text data, according to an embodiment of the present invention;

FIG. 4 is a screen capture for keywords setup, according to an embodiment of the present invention;

FIG. 5 is a flow chart of the three main steps in the text extraction stage, according to an embodiment of the present invention;

FIG. 6 shows a screen capture for extraction results, according to an embodiment of the present invention;

FIG. 7 shows a screen capture for an audit screen, according to an embodiment of the present invention;

FIG. 8 shows a screen capture for an audit screen with incorrect data found, according to an embodiment of the present invention;

FIG. 9 shows a screen capture of an audit screen with the incorrect data of FIG. 8 fixed, according to an embodiment of the present invention;

FIG. 10 is a simplified diagram of the functional design of the graphic data extractor, according to an embodiment of the present invention;

FIG. 11 shows a sample image chart retrieved from a research paper, according to an embodiment of the present invention;

FIG. 12 shows a sample screen capture of the graphic extraction user interface, according to an embodiment of the present invention;

FIG. 13 shows a flowchart of the automatic graphic extraction process, according to an embodiment of the present invention;

FIG. 14 shows a sample digitalized chart before manual adjustment, according to an embodiment of the present invention;

FIG. 15 shows a sample digitalized chart after manual adjustment, according to an embodiment of the present invention;

FIG. 16 shows database schemas for Key Info, according to an embodiment of the present invention;

FIG. 17 shows data categories and application, according to an embodiment of the present invention;

FIG. 18 illustrates database schemas for data sets, data categories and applications in accordance with an embodiment of the invention.

Figure 1A:
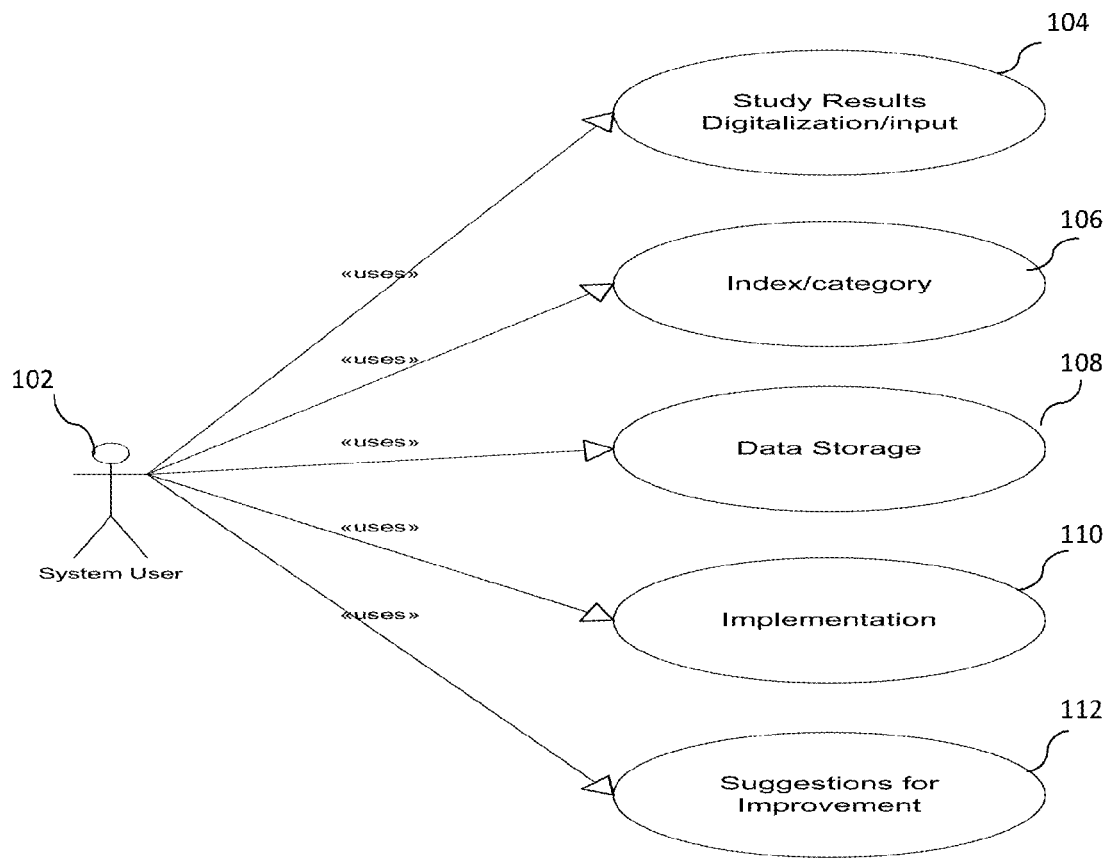
FIG. 1a is a simplified diagram of system use cases, according to an embodiment of the present invention.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

To implement new information (hereafter defined as new info, or new information, for new technologies or new applications of existing technologies), requires the following steps:

Extract the key information (either in text or graph) of the new information into a digital format;

Classify the info into a database with customizable standard categories or key words;

Implement the new info on all related customers' system in large scale networks (such as regional, industrial, state, country or international level).

Currently, there is no system to rapid implement new application from guidelines, standards, studies or publications (such as peer review and acknowledged journals) to the indicated customers through a large scale network. In addition, there is also no system to transfer data file in non-database format into a database format file readily for analysis of customer applications in an automated manner.

Referring to FIG. 1A, this invention provides methods and apparatus of an Automated Information Extraction and Implementation System (AIEIS) 100. It can be used in all industries as a tool. The examples used in the invention are from, but not limited to healthcare. FIG. 1A provides an overview of an automated medical information extraction, implementation and performance improvement at the point of care. In step 104 Key Info are analyzed, digitized, and input to an AIEIS 100. In step 106 the data extracted from the study are indexed and categorized. In step 108 the data is stored in a database. In step 110 the data are implemented. Finally in step 112 the system 100 makes suggestions for improvement.

The system 100 includes the following components: Data Input and Digitization; Index/Category; Data Storage; Implementation; and Suggestions for Improvement/Outcomes.

Data Input and Digitization:

This component uses computer(s) to collect new information directly (numerical) or indirectly (an image-based graph) from a report. There are three possible formats of the new information: (1) the new information are stored in image format which contains one X axis, one Y axis, and one or multiple curves; (2) the new information are stored in text format using a .TXT file, PDF file, and the like. The text documents not only contain the data items for the Key Info but also contain paragraphs of words for explanations; (3) the new information saved as a simple individual data format (such as numerical number, such as 50% improvement or text results, such as change from negative to positive status), easy to be input into database.

Referring to FIG. 2, if the Key Info is already in the format of individual data items easy to be input into database, the AIEIS has graphic user interface to directly input those key info into the Key Info Database 216. If the Key Info is in text format in documents, AIEIS Text Extraction Engine 206A provides tool to search and retrieve the Key Info from the text documents and save them into the database 216. If the study results are in graph format, then the graphs are digitalized into numerical data first using the AIEIS Graphic Extraction Engine 206B and save them into the database 216. The Key Info Database 216 includes 2 parts, the part 1 as Electronic Information Database 216A for the source of the new key information and the part 2 as Electronic Customer Database 216B for the customer or patient info. Both part of the database can be derived from the same process of data extraction 202 using Extraction Engines (206) for text (206A) and Graph (206B). Both part of the database also use the same category, index and application system for classification (see FIGS. 16-18). The purpose of using same extraction and classification is to get the same data/info for comparison in the implementation process for improvement with evaluation and outcome tools.

1. Index/Category:

After new info is digitalized, it has to be indexed or categorized based on current classification of information for specific industry. For example, clinical information is based on ICD (World Health Organization's International Classification of Diseases). For another example, published articles are based on MeSH (Medical Subject Headings, National Library of Medicine). Section 5 describes how to categorize and index the digitalized Key Info. In addition, new categories can be customized (add, delete or revise) by users.

2. Data Storage:

Retrieved new key information is stored into Key Info database 216 based on above classifications. The numerical data is stored using databases, such as (but not limited to) Microsoft SQL Server Database, Oracle Database, etc. Section 5 includes the data schemas inside the database.

3. Implementation:

The AIEIS 100 applies the extracted new information stored inside the external customer databases to the AIEIS Customer database 216B (for example, Computerized Medical Records). These individual customer data in the database, then, is compared with the new information in the Electronic Information Database 216A for further analysis. The implementation service will be discussed herein in section 6.

4. Suggestions for Improvement/Outcomes:

After comparing the customer data with the new information, a customer performance (such as a patient or company) can be assessed and the further improvement can be projected based on the function of the new technology. We provide a description about this component infra.

FIG. 1A illustrates the user interactions with the system. Authorized users may use this system to extract data items from text document and image graphs. After the data items are retrieved, the system will index the numerical data and provides computer database to manage those data. AIEIS has various Internets or Intranets based servers and databases for implementation. Authenticated users may log into the server web site and use those graphs for variety evaluation purposes. AIEIS also provide suggestions for improving customer performance. The following sections give a detailed description about this AIEI System.

5. System Hardware

As will be appreciated by one skilled in the art, the present invention may be embodied as a system, method or computer a combination of program products and a processor device and memory. Accordingly, the present invention may take the form of an entirely hardware embodiment, an entirely software embodiment (including firmware, resident software, micro-code, and the like) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

In this document, the terms "computer program medium," "computer usable medium," and "computer readable medium" are used to generally refer to media such as main memory and secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium.

Computer programs (also called computer control logic) are stored in main memory and/or secondary memory. Computer programs may also be received via communications interface. Such computer programs, when executed, enable the computer system to perform the features of the present invention as discussed herein. In particular, the computer programs, when executed, enable the processor device to perform the features of the computer system. Accordingly, such computer programs represent controllers of the computer system.

Figure 1B:
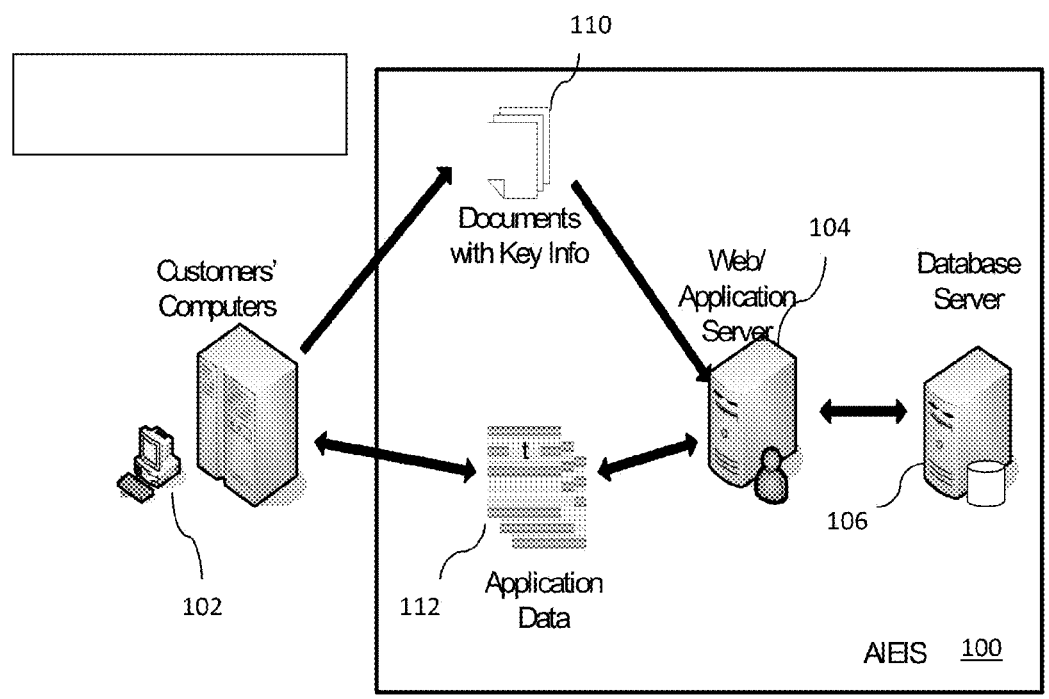
FIG. 1b is an illustration of system hardware configured to perform the method steps according to an embodiment of the present invention.

The AIEIS 100 of the invention is shown in general block-diagram form in FIG. 1b. The customer computer shown in FIG. 1b, illustrated for exemplary purposes as a networked computing device, is in communication with other networked computing devices, the web application server, and the database server. This system has been implemented on two computer servers, including a web/application server 102 and a database server 104. Web/application server allows customers to access the functions of AIEI system through web services. Using graphic web user interface, users may setup extraction rules and data storage requirements, launch extraction processes and view extraction results. Users may also implement the key information into their applications.

As will be appreciated by those of ordinary skill in the art, the network may be embodied using conventional networking technologies and may include one or more of the following: local area networks, wide area networks, intranets, public Internet and the like. For purposes of this invention, the customer computer system shown in FIG. 1B may represent any type of computer, information processing system or other programmable electronic device, including a client computer, a server computer, a portable computer, an embedded controller, a personal digital assistant, and so on.

Web/application server 102 may be implemented on various computer platforms. Windows platforms and Linux platforms or the like are suitable. For Windows, many versions of operating systems can be used, such as Windows XP Server, Windows 2003 Server and the like. For Linux, Redhat v.9 and later are suitable operating systems. Suitable web server software includes Apache servers and Tomcat servers. Suitable code compiling software for data extraction functions including PHP, Java, .Net and others. In this invention, web services are implemented using Windows Server 2003 with service pack 2 and Apache HTTP Server 2.2.4. The .Net programming is used for data extraction functions in this invention.

The Database server 106 in this invention is used to store data about extracted key information, system setup, and customers' applications. In some embodiments, multiple database servers may be used for data replication and to increase the availability of system resources. Suitable database servers include Microsoft SQL Server version 2003 and forward and Oracle Database Server: version 9 and forward. According an embodiment of this invention, Microsoft SQL Server version 2003 is used as data management system.

What has been shown and discussed with respect to the system 100 shown in FIG. 1b is a highly-simplified depiction of a programmable computer system. Those skilled in the art will appreciate that other low-level components and connections are required in any practical application of the system of FIG. 1b capable of performing the described invention.

6. Text Extraction Engine.

Text Extraction Engine 206A is a key component in the AIEIS 100. The inputs of the Text Extraction Engine 206 are: (1) extracted new info from text documents, for example, extrapolation of a new published data of a new technology; or (2) extracted existing data into a format that can be used for an analysis or implementation. For example, extrapolation of existing files (pdf, scanned or XML files) from an Electronic Medical Records (EMR) for analysis or implement the new info using an applicable database. The outputs are the Key Info (hereafter) in a format for: (1). Specific analysis and (2). Database compatible. Usually, it takes a long time to search for new info from those text documents because the text documents not only contain the data items for new info but also contain paragraphs of words for explanations. The Text (Data) Extraction Engine 206A provides a computer aided tool which makes it easy to retrieve Key Info from text documents.

FIG. 2 illustrates functional structure of the Data Extraction 202 in the AIEIS 100. It contains six components: Rule Management 204, Extraction Engine 206 (Text Extraction Engine 206A and Graphic Extraction Engine 206B), Audit Engine 208, Data Management 210, File Management 220, and Graphic User Interface 212.

Rule Management 204.

Generally, text documents contain many paragraphs. Some of those documents have up to a hundred paragraphs with thousands of words. Among those paragraphs and words, very small portion of them is the Key Info to be extracted. The large portion of the document are explanations or support information. Inside the Data Extraction component 202, one module, called Rule Management module 204, is used to define extraction rules about how to find out those small pieces of information from the large information pool. Rule Management module 204 collects extraction rules from a user through graphic user interface 212 and save the rules into pre-defined Rules database 214.

Extraction Engine 206.

Extraction Engine module 206 is the core of the Data Extraction component 202. This module 206 is directly responsible for extracting new info from text documents (or graphic charts 218) and saving the Key Info in numerical formats 216. Extraction Engine 206 reads the text documents (206A) or graphs (206B) from specific file folders 218. After the files are read, Extraction Engines apply the extraction rules 214 to the content of the files. Using the extraction rules 214, Extraction Engine module 206A and 206B retrieve the words (or graph) about new info from the text files (or graphic charts respectively). The further analysis and manipulations will be applied to those words (or graphs). For instance, the words may be converted to standard data format, such as a Boolean value from "yes" and "true" some extra words may be cleaned. Key Info is saved into Key Info database (see FIG. 18).

Audit Engine.

After the Key Info are extracted using the extraction engines 206, the Data Extraction 202 provides an extra function to audit the extracted Key Info against original documents in order to check the accuracy and to further improve the quality of the extraction by revising or adding new rules. Audit Engine module 208 inside the Data Extraction 202 provides an extra protection for the correctness of the extraction. This module reads the extracted Key Info from a database and displays them on the screen for validation. It also links different new info with original text documents. When needed, the original text documents are displayed beside the extracted Key Info for comparison. If a mistake is identified, an update page can be used to revise the extracted Key Info and save the revised Key Info back to the Key Info database.

Data Management 210.

Data Management module 210 gives the function to build a communication channel between the Text Extraction Engine 206A and databases. There are two databases inside the Data Extraction component 202. The Rules database 214 is used to store the extraction rules created by the Rule Management module 204. The Key Info database 216 stores Key Info retrieved by the Extraction Engine 206. Data Management module 210 provides a function to allow a user to specify how to store new info into the database. It also provides a function for a user to define how Key Info being forwarded to external application databases. Based on the settings, the Data Management module will automatically launch data transfer processes. The extracted Key Info may be sent to the application databases for implementation.

Graphic User Interface 212.

The Data Extraction component 202 provides users with a convenient graphic interface for accessing all of the functions discussed above. Using a windows screen, a user may:

find out an original text file (or graph file) and review it;
define extraction rules for the specific type of text documents (or graph documents);
define how to store new info and how to transfer them to application databases;
launch an extraction process and retrieve new info;
display the Key Info and revise it;
revise extraction rules as needed;
revise result storage settings as needed; and
revise result transfer settings as needed.

Extraction Process.

The whole extraction process of Key Info consists of three stages: a. Setup; b. extraction; and c. Audit and revision. A detailed description about those stages is given below.

Stage 1. Setup

The Setup stage has three major steps: define extraction rules; configure data storage; and specify data transfers.

The first setup step is to define extraction. This step comprises three tasks. The first task is to define file format of the text documents (or graph documents) where new info will be extracted. Although many file formats a text document may be in, those formats can be converted into pure text format. Among the files which have pure text format, XML (Extended Makeup Language) file is a special text format which has been widely used for new info documents. XML uses tags to organize a text file. Generally, an XML file contains more characters than non-XML (plain text) file, but is easier to read. In this step, a user should define whether new info is stored inside an XML file or plain text file.

The next task in this step is to define the data items of Key Info. Key Info to be extracted consists of one or more data items. A user has to specify each of data items to be extracted. The Rule Management module is used to specify the following information about each data items: name of data item; Data type: for example, numeric or string; and Value allowed: range for numeric items, bytes for string items, and the like.

The last task in this step is to define extraction rules. As human beings, we also search for some data items based on pre-identified rules. In order to let a computer program to search the data items for us, we need to pass the search rules to the computer program. Various extraction rules can be set into the Data Extraction 202.

The following are some examples.

Keywords. Extraction Engine 206 uses keywords to narrow down search areas for data items of new info. The data item will be located near the keywords.

Positions: Extraction Engine uses Position tags to further narrow down the search areas. For example, "before keywords" or "after keywords" XML tags: for an XML file, XML tags should be defined if a data item is located inside the XML tags. For example, <person><lname> tags can be used to read a person's name.

XML tags and Keywords: if a group of XML tags defines a location which contains more than one data items. Keywords may be added to further locate one of data items. For example, for the following text line in an XML document:

<box>length:32, wide:20</box>

A length value is located by XML tag "box" and keyword "length."

Referring to FIG. 3 there is shown is a screen capture of the Data Extraction 202, according to an embodiment of the present invention. The screen 300 includes a pull down menu 302 that displays a run ETL (extract, transform, and load) command.

Item Relation:

The Data Extraction component 202 provides a Graphic user interface 212 for extraction rule setup. FIG. 4 is an example page for defining keywords. In the case the procedure is a catheterization (CATH). The keyword is shown on the right column.

The second setup step in the Data Extraction component 202 is to configure the storage for new info. The data items extracted have to be stored into New Info database. The Data Extraction component 202 allows a user to configure the Key Info database to save those data items. The following functions have been implemented in the Data Management module 210 and Graphic User Interface 212:

Define and create new database.
Define and create new database table inside the database.
Define, create, and/or update a column inside the database table The last setup step is to specify Key Info transfer. The Key Info extracted will be implemented into external applications. The Extraction Engine 206 A and B have a built-in function which is used to forward the extracted new info to external applications. In order to do that, Data Management module 210 has to know:

How the data item of new info should be transferred. "Using XML" is one of the supported options; "To Database" is another option.

Where those applications are located. For the "Using XML" option, the following information items have to be specified: network IP address, port, authentication, encryption, etc. For the "To Database" option, we need to define: database location, database name, authentication, encryption, etc.

When the data items of new info should be transferred. "Transfer Now" is one of the supported options; "Transfer when updated" is another option.

Those information items can be specified using Data Management module 210 and Graphic User Interface 212.

Stage 2. Data Extraction

The Data Extraction stage has three major steps as shown in FIG. 5. The first step in this stage is to select pre-defined settings 502 for the extraction process, including extraction rules, storage configurations, and data transfer settings. Different text documents are categorized into multiple groups and sub-groups based on the content structures. For every group, a set of rules, configurations and settings should be created in the previous step 502. A user has to select 504 a special set from the list and make sure the set is defined for the text documents the new info extracted from.

After the rule set is selected 504, the user needs to specify the text document(s) to be extracted from. There are two possible options for this step. One is individual document process. The other is batch process. For individual process, a user selects a text document from File Selection dialog box inside the Graphic User Interface module. For the batch process, the user selects a file folder. All the files inside the folder will be process.

Now, we can start the automatic extraction process 506. The following tasks are automatically finished by the Extraction Engine module inside the Data Extraction: Read text documents; Read Extraction Rule set; Apply the extraction rules to read date items of new info; and Save the data items into the Key Info database.

FIG. 6 shows a screen capture 600 for extraction results, according to an embodiment of the present invention.

Stage 3. Audit and Revision

After the data items for Key Info are extracted by the Extraction Engine 206, a user may need to verify the accuracy of the extraction and correct possible mistakes. This will be the last stage for the new info extraction, the Audit and Revision stage. The Data Extraction 202 has a built-in Audit Engine with computer-based graphic user interface, which makes this task easier than manual audit processes. FIG. 7 shows a computer screen capture 700 for this stage.

The first step in this stage is to specify a group of data items of new info by selecting some search filters, including the name of new info, date range of the data items being extracted. Audit Engine module inside the Data Extraction 202 reads the data items from New Info database based on the search filters and display the data items into a list (see the left hand side in FIG. 7).

Each line of the data items in the list is read from one text document (or a group of related text documents). By double-clicking the line of data items, the original text documents can be retrieved and displayed on the same screen using pop-up windows (see one XML file on the right hand side of FIG. 7). A user may move the documents around for viewer convenience.

Inside a text document, Audit Engine module 208 and Graphic User Interface module 212 will highlight all the locations where the data items of new info are read from. When a data item is double clicked, the window of the original text document will be moved to the top of all the windows. The cursor of the window will be moved to the location where the data item is extracted. A user may be easy to check the correctness of the data items.

If a mistake is found (EF, ejection fraction, value: 45 in FIG. 8), the user may highlight the data value from original text document and update the data items inside the list using window's Copy/paste function. The revised data items (EF value: 55 in FIG. 9) can be saved into New Info database using the Save function provided by the Audit Engine module 208 and Graphic User Interface module 212. Those modules also provide functions for creating new data item and deleting existing data items as needed.

Graphic (Data) Extraction Engine

Graphic Extraction Engine (206B) is a key sub-component in the AIEIS 100. Many Key Info with image graphs contain axes and curves. Using the axis and curves, the image graphs illustrate important study findings. The functionality of the Graphic Extraction Engine is to convert those image graphs to numerical data and store the data into computer database for future use (such as reports, comparisons and calculations). Graphic Extraction Engine provides automatic extractor and graphic user interface (UI) to convert those image charts. Graphic Extraction Engine can be configured to cover different types of image graphs. FIG. 10 illustrates the components in the Graphic Extraction Engine and the relations among those components.

The chart digitalization in this system includes the following three steps: Input Images; Automatic Graph Extraction; and Editing and Fine Tuning.

Step 1: Input Images

The first step of chart digitalization is to input a graph chart into the system 100. The Digitalization system 100 takes publications in electronic formats (such as PDF or Doc format) as input. A user may use a mouse to select a chart from a published paper, capture the graph and convert into an image file. The image file can be saved into a well-known image format. This system supports most of commonly used image formats, such as BMP, JPG, GIF, and the like. Each image file may contain a simple line graph plotted on x and y axes. The system also supports multiple lines inside one image file, even if they intersect or overlap at certain points.

FIG. 11 is a sample image 1100 which has been input into the system. An image graph 1100 has the following key elements be digitalized.

Axis.

Axis 1102 contains the starting and the end point of the identity of the axis, such as X or Y axis. Since an axis is either horizontal or vertical, only one X or Y value is needed to record corresponding position information.

Curve.

A numerical curve 1104 consists of series of (x, y) pair datasets. Each curve is also coded with different Color for separation. Each curve on a chart has a unique ID.

Graph.

Graph contains axis and list of curves.

Step 2: Automatic Extraction

Graphic User Interface 212.

This system 100 provides a graphic user interface 212 to digitalize a graph chart. The interface supports both automatic extraction and manual editing for fine tuning It is easy to use. The user does not need any digitalization knowledge. FIG. 12 shows a sample screen capture of the graphic user interface for the Graphic Extraction Engine.

Load Chart Image

The first task of Automatic Graph Extraction is to load the graph chart into the AIEIS 100. As previously mentioned, the input file can be in a number of formats, such as JPG or the like. Those image formats has to be converted to RGB color model in order to detect color of chart elements. RGB is an acronym for Red, Green, and Blue. RGB is a convenient color model for computer graphics. The color of an image point can be identified using the values of R, G, and B at that point.

Auto-Extract Image.

The working flow of auto-chart extraction is shown in FIG. 13. This section gives more details about how the system automatically extracts the graph charts.

Detect a Valid Drawing Point

A graph contains multiple drawing lines. Basic function of Graph Extraction is to identify valid drawing lines which build axes and curves. A valid drawing line consists of multiple drawing points. The following rules are applied in order to detect a valid drawing point which belongs to axes or curves.

A drawing point has a solid color which is significantly different from white color (R=255; G=255; B=255). A configurable cut-off value u (default to 230) is used to check the difference. Any point with solid color must have at least one of RGB values less than u (R<u or G<u or B<u);

A drawing point may contain multiple graph pixels. A configurable value is used to define how many graph pixels a drawing point contains;

The drawing point on an axis or a curve must be connected with another drawing point with the same color.

X and Y Axes Extraction

To start off, the x-axis and y-axis are automatically detected using the following algorithm.

X Axis Extraction Algorithm:

Step 1302 scans the entire chart from bottom to top. For each line, it scans each pixel from left to right. If a pixel has RGB values less than predefined values, the pixel counts a color pixel. If a line contains continuous pixels with the same color, this line is counted as a candidate of X axis. Remember the length of each candidate.

Group the candidates based on continuity. Choose the group of the candidates with the longest average length. Pick the most top candidate from this group as the X axis. The method then checks the digitization process in step 1304. If the result is positive then the method continues at step 1306 and it is negative the method returns a failure 1316.

Y Axis Extraction Algorithm:

Step 1306 scans the entire chart from left to right. For each line, it scans each pixel from bottom to top. If a pixel has RGB values less than predefined values, the pixel counts a color pixel.

If a line contains continuous pixels with the same color, this line is counted as a candidate of Y axis. Remember the length of each candidate. Group the candidates based on continuity. Choose the group of the candidates with the longest average length.

Pick the topmost candidate from this group as the Y axis. The method then checks the digitization process in step 1308. If the result is positive then the method continues at step 1310 and it is negative the method returns a failure 1316. These axes are then immediately highlighted in blue on the screen for the user to confirm their locations.

The user also has the option to manually position the axes, overriding the software's auto-extracted positions. A user may manually position the axes using the Graphic Extraction Engine 206B and Graphic User Interface 212.

Create an X axis using GUI: Select Add X Axis sub-menu from Edit menu. Click the start point of the X axis on computer screen. Click the end point of the X axis on computer screen. Graph Extraction Engine will mathematically interpolate between the start point and the end point to obtain continuous numerical values for the X axis. The data is saved into computer database.

Create a Y axis using GUI: Select Add Y Axis sub-menu from Edit menu. Click the start point of the Y axis on computer screen. Click the end point of the Y axis on computer screen. Graph Extraction Engine will mathematically interpolate between the start point and the end point to obtain continuous numerical values for the Y axis. If data is saved into computer database. Success in the digitization is then checked in step 1312. If the result is positive the method is finished in step 1314. If the result is negative then a failure is achieved in step 1316.

Curve Extraction

In step 1310 the program will then attempt to detect the line curves themselves in the following manner. First, the user is asked to input the number of curves to detect. Then, the program scans the entire chart to detect every curve using the following Curve Extraction algorithm.

The method scans every vertical line in the entire chart from left to right. For each vertical line: Scan each pixel from bottom to top. If there is a color pixel, it is counted as a pixel on a curve. On each vertical line, filter out those continuous color pixels that are above the previous color pixel if we want to find a color pixel for another curve.

The color of a curve will be the color of the first color pixel found on that curve. After that, only pixels whose color is close enough to the color of the curve are considered. After all vertical lines have been scanned, remove isolated color pixels and link the continuous color pixels from left to right.

Step 3: Editing and Fine Tuning

The program also allows for manually editing to fine-tune the detected curves before data points are finalized in step 1314. This is particularly useful because charts can be formatted in any number of ways, some that might interfere with the image processing algorithms employed by the software. In these cases, the user may want to manually step in to assist in the curve position definition process and provide the suggested correction to the system 100.

Adjustment of Data Points

One way in which the user can fine-tune the curve is by adjusting some of the data points. The original data points detected by the program are first superimposed on the input graph. The user can click on the indicating marker for each data point and drag it with the mouse cursor to any desired location.

FIG. 14 and FIG. 15 illustrate an adjustment process for a sample image for research paper. An image chart captured from a research paper may contain some color "noise". The auto-extraction process occasionally picks up a few wrong data point due to some color "noise". FIG. 14 shows a sample result after an auto-chart extraction. It can be seen that there are two wrong data points (at middle of the grey curve) 1402 picked up by the auto-chart extraction. Graphic Extraction Engine provides the function for user to view and correct those wrong data points using graphic tools. A user may drag a wrong point and move it to a desired location using mouse. FIG. 15 shows the results after the two wrong data points are corrected using the Fine Tuning function.

Adding New Data Points

New data points can be added as well in the event that critical point on the graph was not captured by the automatic detection at all. The user can simply drag a marker to the desired point.

Delete Existing Data Points

Extraneous data points can be deleted from the chart with a simple click.

Data Storage for Digitalized Graph

The following parameters of Key Info are collected and stored into database. Title of chart: One digitalized image chart will be given a title. The title is used to uniquely identify the chart within the database. Axis: include two start points and two end points.

Axis X: $(X_{sp1}, Y_{sp1})$, $(X_{ep1}, Y_{ep1})$

Axis Y: $(X_{sp2}, Y_{sp2})$, $(X_{ep2}, Y_{ep2})$

Curve: include multiple points $(X_{p1}, Y_{p1})$, $(X_{p2}, Y_{p2})$, ... $(X_{pn}, Y_{pn})$ Parameters: reference information about where the chart comes from, such as author, publish date, publish name, page number, and the like.

Indexes

FIG. 16 shows the database schema for digitalized Key Info.

Data Category and Indexing

Now, the Key Info has been extracted into numeric data sets, the data items must be stored for future use. Before data is stored, it has been categorized and index. Both Data Category and Indexing are used to improve the efficiency of searching and retrieving the data set, which make the data implementation easy.

Data Categories

An authorized user may create data categories using the AIEIS web services. The AIEIS supports multiple ways to create data categories. One of common used methods is to group the digitalized new info into categories and sub-categories based on data applications, as shown in FIG. 17. Each category or sub-category has its own data set which represents the digitalized new info for one group of data applications. When a group of users wants to apply the data set into their new applications, they may choose the data set from one data category or sub-category.

The AIEIS provides Data Management module 210 and Graphic User Interface 212 to help users manage data categories and applications. The management tools contain the following functions:

Create/update/delete data categories {C} and sub-categories {S}.{C} or {S} denotes a mathematics set of data categories or sub-categories:

$\{C\}=\{C_1, \ldots, C_{n1}\}$
$\{S\}=\{S_1, \ldots, S_{n2}\}$

Add a data set into a data category or sub-category after the data set is extracted using Text Extraction Engine or Graphic Extraction Engine Create/update/delete application into one data category or sub-category.

The relationship among data set, data categories and applications is stored into the New Info database. FIG. 18 shows the database schema. Database table 'Data category' stores the relations among data category or sub-category. Data sets of new info are stored into database table 'Chart' and database table 'Text_data'. Database table 'Chart' saves the data extracted from a graph. Database table 'Text_data' saves the data extracted from a text source. Information about the new applications is stored into database table 'Application'.

Data Indexing

The index is used to group specific Key Info, which makes digitalized new info easy to be searched and implemented. A data index is a data structure that enables sub-linear-time data search to data storage. The AIEIS 100 has multiple built-in index tables which index the numeric data sets using the following parameters:

Related application factors: Several factors can be used to characterize the applications of a new info, such as key words, application names, original author names, and publish date, etc.

The index or category can be based on current classification of information for specific industry. For example, clinical information is based on ICD (World Health Organization's International Classification of Diseases). For another example, published articles are based on MeSH (Medical Subject Headings, National Library of Medicine). Section 5 describes how to category and index the digitalized Key Info. In addition, new categories can be customized (add, delete or revise) by users.

Implementation of New Info for Improvements.

There are two categories of inputs into the system: (1) new info from a new study; (2) existing info from previous reports in customer data storage (such as EMR (electronic medical records)). Newly available information might come in the form of new scientific articles, reports, and any sort of released quantitative information. The second category of inputs is existing data which is stored in archived documents. Within these documents, the Key Info deemed important but embedded within large bodies of text used to be difficult to be analyzed because the Key Info is not in database format, hard to be searched and retrieved. Using this invention, the data has been extracted into computer database and indexed. Being able to extract and efficiently store quantitative data allows us to isolate the most critical information from possibly bulky documents.

The implementation cases are numerous. This information can be aggregated from the database for immediate numeric recall, or for more macroscopic analyses. For immediate recall, the goal is to retrieve the value for the response variable (or system output) given fixed inputs for a set of explanatory variables. The relationships between the inputs and the response variable are usually extracted from text or graphic documents, such as scientific articles, research papers, etc. An authorized user retrieves those relationships from the database. Using those relationships, a response variable can be matched out for a group of fixed inputs {FA} for a set of explanatory variables.

response variable: RV=relation({FA})

Figure 19:
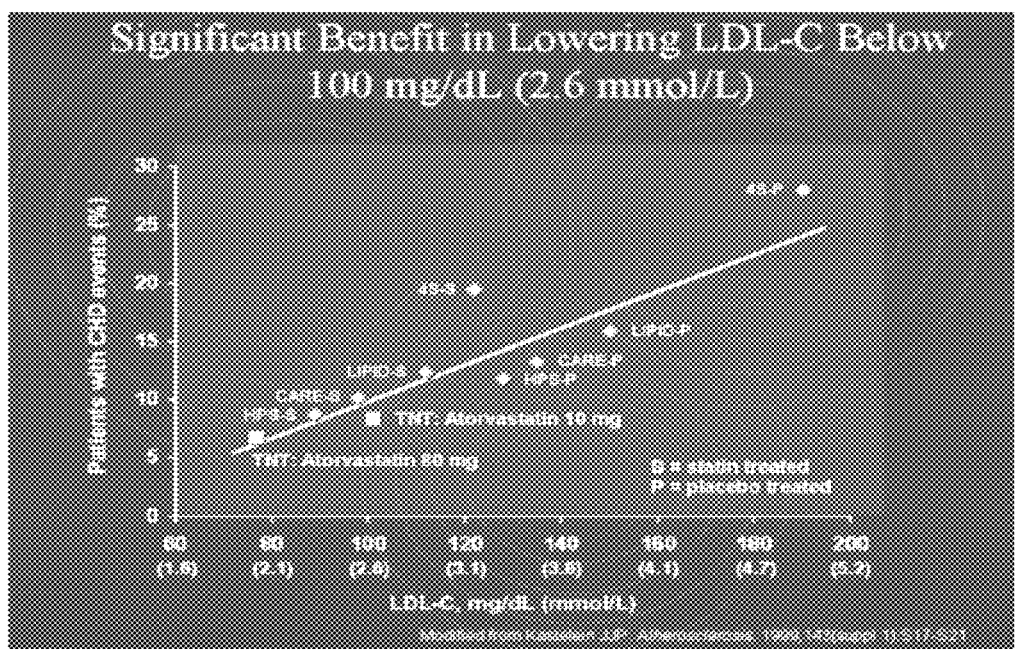
FIG. 19a is a chart showing data output, according to an embodiment of the present invention.
FIG. 19b is a chart showing a use for the output of FIG. 19a, according to an embodiment of the present invention.
Figure 19:
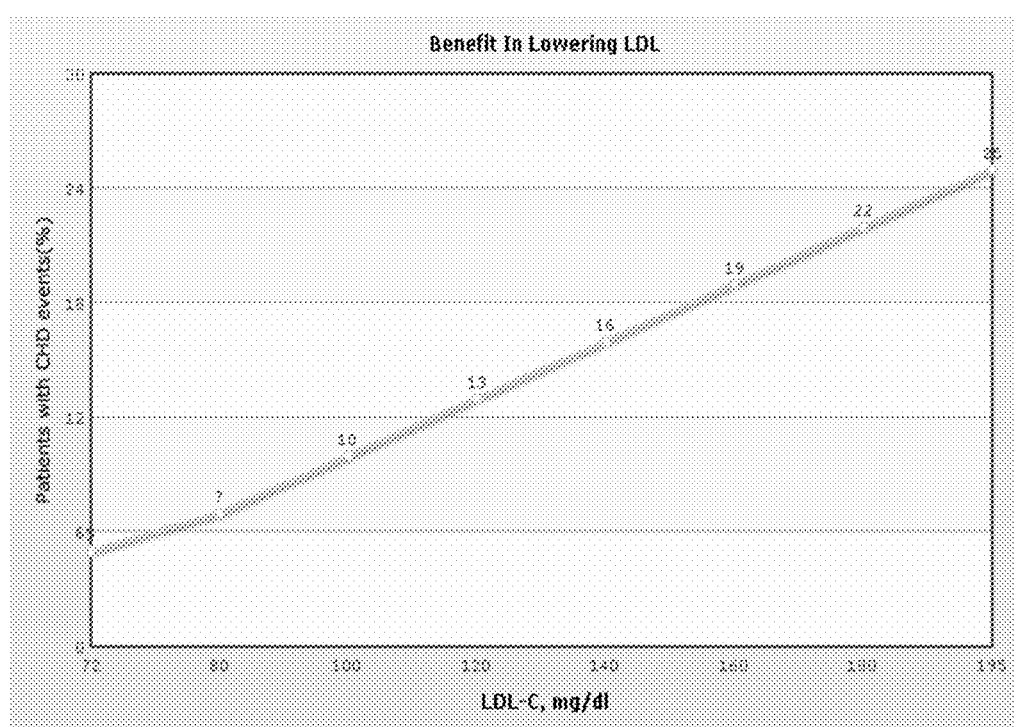

For instance, to implement a LDL treatment strategy to decrease coronary heart disease (CHD) event (heart attack and death), one can use the AIEIS Graphic Extraction Engine to digitize the new info from a published study file in pdf format (FIG. 19A) into a Key Info in digital database format. The new strategy suggests that CHD event rate can further decreased from ~14% (LDL level 130 based on current NCEP cholesterol treatment guidelines) to 7%, if use statins to reach LDL 80).

Macroscopic analyses can also be conducted based on pulling out processed data in aggregate. The processed data is usually retrieved from accumulated text reports, such as financial reports for a company, medical records for a group of patients, etc. An authorized user retrieves the key info from the database and then applies some Macroscopic analyses to those data items {DI} in order to evaluate system outcomes.

System outcome: OC=function({DI})

Using the above LDL example, all patients with LDL level above 130s can be identified from a customer database, or extracted from storage files using current AIEIS.

Outcomes

The final outcomes of the implementation of a new info in the real world can be linked with an Outcome-based tracking and analysis system, which has been described elsewhere.

Security:

The AIEIS 100 has control features for users to implement digitalized Key Info. For examples:

Privacy control: A user may set: who can access the Key Info, when the Key Info can be implemented, and how they can be accessed.

Triggers control: A user may define a schedule about how often the Key Info should be implemented. For example, a user may want to apply the Key Info every day. Then, every day, the AIEIS 100 will send the user an implementation/suggestion report. A user may also define some event. When the event occurs, the AIEIS will automatically implement digital Key Info and send the user an implementation/suggestion report.

Report control: A user may specify to whom an implementation/suggestion report will be sent.

Industries:

Any industries use new study or research on new technology or new applications of old technology to improve current performance, for example, but not limited in the following: Health Care; Computer applications; Electronic manufacture and applications; Finance; Law enforcement; Pharmaceutical; Airline and services; Media; Government; Marketing; and Sales.

Related Systems and Network: Any large system with large scale customers can be benefited to implement new results/technology to improve their outcomes immediately. Benefits may be derived in Computerized Medical or Health Records; Industry networks; and any large scale system network such as regional or national network.

The invention claimed is:

1. A computer implemented method for information extraction and patient performance assessment comprising:
   receiving documents for analysis, the documents including key information in both text and graphic format related to standards of medical care;
   in an application server:

generating rules for key information indexing, extraction, conversion and storage
searching the documents for the key information and extracting the key information;
verifying and editing the key information
indexing the key information;
storing the key information into a key information database of a database server based on the indexing;
in the application server, extracting or importing patient key information from a group of patients having common indexes based on the extracting rules
implementing the key information extracted from the documents of medical standards to patient(s) key information to assess patient(s) performance and outcomes.

2. An automated method for medical information extraction, implementation, and performance assessment for purposes of patient care improvement, said method comprising:
in a large-scale distributed network, performing:
providing a user interface configured to generate rules for data extraction, data conversion, and data storage of key information comprising standards of medical care;
receiving data extraction parameters and data conversion parameters defined by the user;
storing the data extraction parameters and the data conversion parameters into a key information database according to storage parameters defined by the user;
using a processor device in a first system, performing steps of:
isolating the key information from a document;
extracting only the key information according to the data extraction parameters, wherein said key information is in a form of at least one of: text and graphic chart data;
presenting the extracted data for auditing and editing on the user interface;
converting the graphic chart data by digitalizing said graphic chart data into numerical data according to the data conversion parameters, when the extracted data has been verified;
storing the extracted data into the key information database; and
transferring the extracted data to external applications for implementation; and
using a processor device in a second system, implementing the extracted data by performing steps of:
extracting a plurality of medical records data from at least one medical records database;
accessing the key information database;
comparing the extracted medical records data to the converted data stored in the key information database; and
assessing an outcome of the comparison based on the key information, wherein said outcome indicates whether the standards in medical care are being met.

3. An information processing system for automated medical information extraction, implementation, and performance assessment for purposes of patient care improvement in a large-scale distributed network, said information processing system comprising:
a memory with computer-executable instructions stored therein, said computer-executable instructions comprising:
providing a user interface configured to generate rules for data extraction, data conversion, and data storage of key information comprising standards of medical care;
receiving data extraction parameters and data conversion parameters defined by the user;
storing the data extraction parameters and the data conversion parameters into a key information database according to storage parameters defined by the user;
isolating the key information from a document;
extracting only the key information according to the data extraction parameters, wherein said key information is in a form of at least one of: text and graphic chart data;
presenting the extracted data for auditing and editing on the user interface;
converting the graphic chart data by digitalizing said graphic chart data into numerical data according to the data conversion parameters, when the extracted data has been verified;
storing the extracted data into the key information database; and
transferring the extracted data to external applications for implementation;
a processor device in a first system operably coupled with the memory and executing the computer-executable instructions; and
a processor device in a second system operably coupled with a second memory and executing computer-executable instructions comprising:
implementing the extracted data by performing steps of:
extracting a plurality of medical records data from at least one medical records database;
accessing the key information database;
comparing the extracted medical records data to the converted data stored in the key information database; and
assessing an outcome of the comparison based on the key information, wherein said outcome indicates whether the standards in medical care are being met.

* * * * *